United States Patent [19]

Broughton et al.

[11] Patent Number: 4,585,011
[45] Date of Patent: Apr. 29, 1986

[54] CONJUGATE EYE MOVEMENT DETECTOR FOR SLEEP ANALYSIS

[75] Inventors: Roger Broughton; Bernardo da Costa, both of Ottawa, Canada

[73] Assignee: Canadian Patents & Development Limited, Ottawa, Canada

[21] Appl. No.: 659,297

[22] Filed: Oct. 10, 1984

[30] Foreign Application Priority Data

Oct. 14, 1983 [CA] Canada ................................ 439063

[51] Int. Cl.$^4$ .............................................. A61B 5/04
[52] U.S. Cl. .................................... 128/733; 128/745
[58] Field of Search .............. 138/731, 733, 745, 774, 138/782, 901, 902

[56] References Cited

U.S. PATENT DOCUMENTS 3,548,812  12/1971  Paine ................................... 128/731
4,359,724  11/1982  Zimmerman et al. .............. 128/733

OTHER PUBLICATIONS

Bremer et al, "Automatic Detection of the K-Complex in Sleep Electroencephalograms," IEEE Transactions on Biomedical Engineering, vol. BME-17, No. 4, Oct. 1970.
Debecker et al, "Automatic Suppression of Eye Movement and Muscle Artifacts When Averaging Tape Recorded Cerebral Evoked Potentials," Electroencephalography and Clinical Neurophysiology, vol. 37, No. 6, Nov. 1974.
Thomas et al, "Transducer for Recording Fine Eye Movement Through the Closed Eyelid," Medical & Biological Engineering & Computing, Nov. 1977.
D. Green, "A Hybrid Pre-Processor for Sleep Staging Using the EEG, 1977, Ch. 7, pp. 1-13, Ch. 9, pp. 1-10.
Gaillard & Tissot, "Principles of Automatic Analysis of Sleep Records With a Hybrid System," Comp. Biomed. Res., 1973, 6: 1-13.
R. Broughton et al, "A Phase-Locked Loop Device for Automatic Detection of Sleep Spindles and Stage 2," Electroencephalography and Clinical Neurophysiology, 1978, 44: 677-680.

Primary Examiner—Edward M. Coven
Assistant Examiner—Daniel Haneiwich
Attorney, Agent, or Firm—Edward Rymek

[57] ABSTRACT

The eye movement detector detects events occurring during the electro-oculogram (EOG) signal in which components of the signal having a predetermined rise time, are coincident with components of the same signal having a predetermined amplitude.

3 Claims, 2 Drawing Figures

CONJUGATE EYE MOVEMENT DETECTOR FOR SLEEP ANALYSIS

BACKGROUND OF THE INVENTION

This invention is directed to automatic sleep analysers and, in particular, to detectors for the specific events used in staging sleep.

A scoring system for staging the sleep patterns of adult humans has been standardized, and is described in the manual edited by A. Rachtschaffen and A. Kales entitled, "A Manual of Standardized Terminology, Techniques and Scoring System for Sleep Stages of Human Subjects". "Public Health Service, U.S. Government Printing Office, Washington D.C. 1968—National Institutes of Health Publication No. 204".

In scoring sleep, three basic signals recorded as electrical activity in the body, are required. These are the activity of the brain, the eyes and the muscles. The activity of the brain is represented by an electroencepholographic (EEG) signal obtained from electrodes placed on the head. The activity of the eyes is represented by electro-oculo-graphic (EOG) signals obtained from electrodes placed near each eye. The muscle tone activity is represented by an electromyographic (EMG) signal obtained from electrodes usually located under the chin.

The activity signals would normally be recorded on a paper printout, and divided into time segments or epochs, e.g. of forty seconds. Specific events are noted visually during each epoch in order to classify that epoch as a certain state of sleep or non-sleep. The conventional seven states of sleep or non-sleep are known as wakefulness, stage 1 sleep, stage 2 sleep, stage 3 sleep, stage 4 sleep, REM sleep and movement time. These are listed in Table 1 together with the criteria for each epoch state used in the classification. The events used to stage or classify these states are alpha rhythm, sleep spindles, delta activity, and movement artifact which are observed in the EEG signal, rapid eye movements (REM) which is observed in the EOG signal, and muscle tone which is observed in the EMG signal.

TABLE 1

| | Criteria for Sleep Staging | | | | | | |
| --- | --- | --- | --- | --- | --- | --- | --- |
| | State | | | | | | |
| Event | W | 1 | 2 | 3 | 4 | REM | M.T. |
| Alpha | ± | 0 | 0 | 0 | 0 | ± | ± |
| Spindles | 0 | 0 | + | ± | ± | 0 | ± |
| Delta | 0 | 0 | <20% | 20–50% | 50–100% | 0 | ± |
| Mov't artifact | ± | 0 | 0 | 0 | 0 | 0 | >50% |
| REM | ± | 0 | 0 | 0 | 0 | + | ± |
| EMG | + | ± | ± | ± | ± | 0 | + |

Table 1 lists the events and their levels which are to be observed during an epoch in order to classify it into a particular state. However, in addition to this table, certain guidelines exist for staging sleep by which the state in each epoch can only be determined by observing events that occur in previous or subsequent epochs.

Traditional sleep recording with a monitoring technologist is very time consuming and expensive, involving overnight shift work and slow visual analysis of very long paper recordings. The need for a monitoring technologist can be avoided and, in many cases, be replaced by using portable recordings placed on the subject to record the required signals continuously in his normal home environment. The slow visual analysis of long paper recordings can be circumvented by the use of automatic analysis, at high speed playback, of tape recorded data from either portable or traditional in-laboratory recordings. Automatic analysis can replace such long recordings by summary statistics and charts, and also improve scoring consistency.

A number of centers have attempted various approaches to automatic sleep analysis as a particular extension of the problem of automatic EEG analysis. Sleep EEG events have most frequently been detected by spectral analysis, by pattern recognition, and by period analysis of zero-crossing data. As well, digital filters have recently been introduced and have potential application in the field. Combinations of these methods have sometimes been used to detect individual sleep EEG events which combine zero-crossing analysis with an amplitude criterion, a period discriminator to determine frequency band (delta, alpha, spindle, beta or muscle potential), plus a pattern criterion. The staging of sleep may be done using detectors based on the above approaches which are then combined in a "hard-wired" processing unit. Alternately, all data processing for sleep staging may be done by a large general purpose computer. The hard-wired sleep stagers have the advantage of lower cost, but the great disadvantage of being inflexible. Performing all analyses on digitalized raw data in a necessarily large general purpose computer, on the other hand, is very expensive.

An intermediate approach, in which the present invention is used, has a series of (sometimes modifiable) event detectors as part of a preprocessor unit. The detectors detect essentially only those events which are used for visual analysis. Their outputs can then be analysed for quantification of sleep variables and for sleep staging, either visually, or automatically by a microprocessor or a small general purpose computer. Gaillard and Tissot have chosen a somewhat similar approach, as described in their publication, "Principles of automatic analysis of sleep records with a hybrid system", Comp. Biomed. Res., 1973, 6:1–13. In this system the outputs of a preprocessor consisting of 12 bandpass filters for EEG analysis, an eye movement analyser, a muscle integrator, an EKG counter, and a galvanic skin response (GSR) counter are coupled to a small general purpose computer. Such an approach combines the advantages of relatively low cost and flexibility.

As described above, the events to be detected are alpha rhythm, sleep spindle, delta activity, and movement artifact in the EEG signal, plus REMs and muscle tone.

The alpha rhythm in automatic sleep analysers is generally detected using a classical bandpass filter or zero-crossing detector and a level discriminator. A particularly useful phase-locked loop alpha detector is described in the thesis entitled, "A Hybrid Pre-Processor for Sleep Staging Using the EEG", by D. Green, 1977, Chapter 7, pp. 1 to 13. This detector produces an output, when the EEG signal has a component with a frequency of 8–12 Hz at greater than 25 $\mu$V peak-to-peak amplitude.

The sleep spindle is the sleep EEG event most comprehensively examined to date. The approaches to spindle detection include: zero-crossing methods, classical analogue bandpass filtering, bandpass filtering with harmonic analysis, a software Fast Fourier Transform (FFT) approach, a matched filter approach, and a phase-locked loop (PLL) approach. A highly accurate sleep spindle detector is described in the publication by R. Broughton et al, entitled "A Phase-locked Loop Device for Automatic Detection of Sleep Spindles and Stage 2", Electroencephalography and Clinical Neurophysiology, 1978, 44:677–680. This detector produces an output when the EEG signal has a component with a frequency of 11.5–15 Hz at greater than 14 μV peak-to-peak and a minimum burst duration of 0.5 seconds.

Delta activity detection can be performed by using analogue bandpass filters with energy detectors, by zero-crossing analysis using amplitude and period criteria, or by a software approach. A particularly useful delta detector which detects components of the EEG signal having a frequency of 0.5–1.5 Hz at greater than 67 μV peak-to-peak, is described in the above noted thesis, chapter 9, pp. 1 to 10.

Of the three remaining event detectors required for sleep analysis, a Muscle Tone Detector and a Movement Artifact Detector are described in copending U.S. patent application Ser. Nos. 659,296 and 659,295 (now U.S. Pat. No. 4,550,736) respectively filed on even date herewith by R. Broughton et al.

SUMMARY OF THE INVENTION

It is therefore an object of the present invention to provide a conjugate eye movement detector for a sleep analyser.

This and other objects are achieved in a detector which receives the electro-oculogram (EOG) signal, selects components of the EOG signal which have a predetermined rise time, and selects components of the EOG signal which have a predetermined amplitude. The detector then produces an output pulse each time a predetermined rise time component is coincident with a predetermined amplitude component in the EOG signal. The EOG signal may be a combined left eye EOG signal and a right eye EOG signal to provide greater reliability.

The predetermined rise time components may be selected by a band-pass filter having a real time frequency band from 1.3 to 5.4 Hz. The predetermined amplitude components may be selected by positive and negative threshold discriminators each connected to one input terminal of an or-gate.

Many other objects and aspects of the invention will be clear from the detailed description of the drawings.

DETAILED DESCRIPTION

Figure 1:
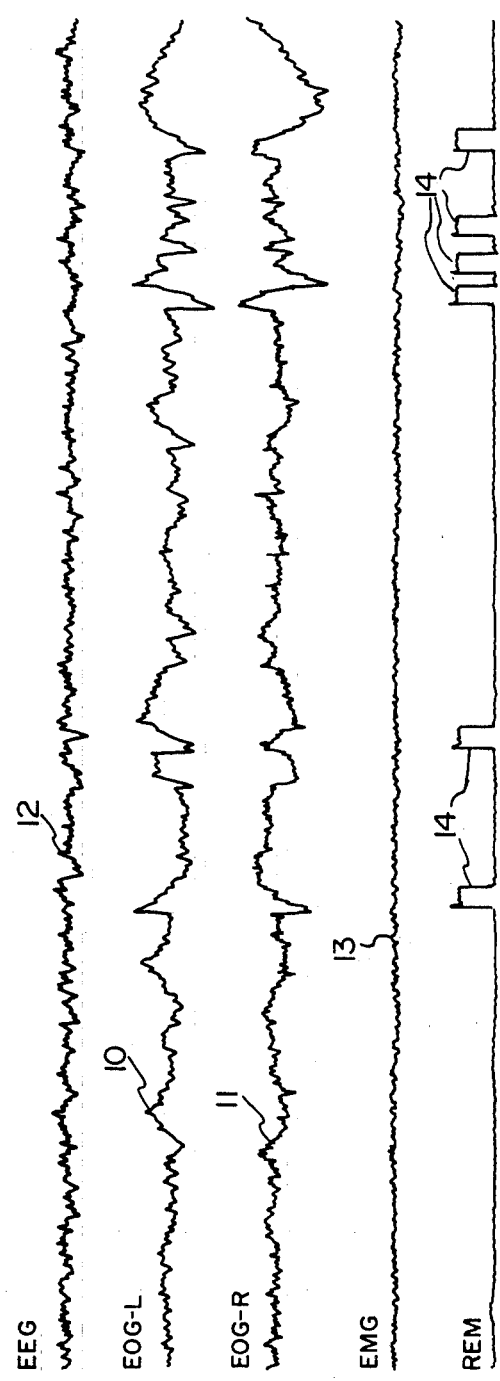
FIG. 1 illustrates the EEG, EOG, and EMG signals used in sleep analysis plus the output of the conjugate eye movement detector.

The conjugate eye movement detector operates on the electro-oculogram (EOG) signals obtained from electrodes placed at the side of each eye. The signals are usually preamplified and recorded in real time on two channels of an EEG apparatus or a magnetic tape recorder. As shown in FIG. 1, the signals of the left eye recording 10 and the right eye recording 11 are very similar though inverted. Rapid eye movement signals are normally in synchrony, though on occasion, the eyes will wander out of synchrony, as in slow eye movements in drowsiness. The remaining recordings in FIG. 1 are the electroencephalogram signal 12 and the electromyogram 13.

An eye movement detector, in accordance with this invention, will therefore preferably be made to detect rapid eye movements in which the two eyes move in synchrony and in the same direction, i.e. such that their electric signals are inverted relative to one another. In addition, it has been determined that in order to detect REM signals consistently in accordance with the Rechtschaffen and Kales standards, the component of the EOG signal to be detected should have a real time frequency of 1.3 to 5.4 Hz and an amplitude of at least 38 μV. These criteria are consistent with the speed at which the eyes should move as well as the distance they should move to be considered to be an REM event.

In order to save analysis time, the EOG signals may be fed to the detector at a much greater speed than that at which they were recorded. The detector will be described in terms of real-time parameters, the actual parameters of the detector will, of course, depend on the actual speed at which it is designed to operate.

Figure 2:
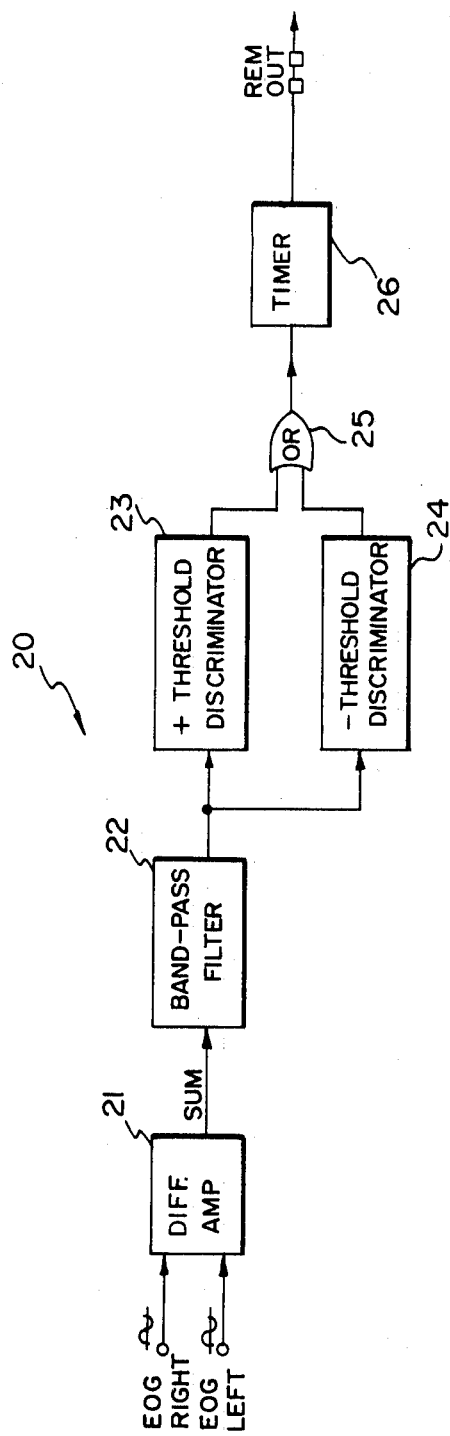
FIG. 2 is a schematic of an eye movement detector in accordance with the present invention.

All of the above criteria are met by the detector 20 illustrated in FIG. 2, in which the EOG right signal and the EOG left signal are fed to a differential amplifier 21 which effectively inverts one of the inputs and then sums the two signals. The summed signal is fed through a bandpass filter 22 which limits the output signal to a real time frequency of 1.3 to 5.4 Hz. The output signal will therefore have a predetermined risetime. The filtered signal is fed to a pair of discriminators 23 and 24, the former having a preselected positive threshold and the latter having an equivalent negative threshold. The outputs from the discriminators 23 and 24 are connected to an "or" gate 25, whose output controls a timer circuit 26 which produces constant width pulses in response to the EOG signals containing REM activity. The timer 26 is set to produce fixed width pulses. FIG. 1 illustrates the pulses 14 produced at the output of eye movement detector 20.

As mentioned above, the eyes normally move in synchrony and, therefore, the signal from one eye would normally be sufficient to determine rapid eye movement. However, by combining the signals from the left and the right eye, the threshold discriminator 23 and 24 can be set so as to detect eye movement only when both eyes move in one direction and thus provide greater accuracy. This approach also reduces artifactual false positive REM detections, which occur if only one channel is used and which are due to sources other than eye movements, such as EEG signals picked up by the EOG electrodes.

Rise time and amplitude may be detected sequentially as in the embodiment in FIG. 2, however, they may also be detected in parallel or in the reverse sequence, i.e. amplitude and then rise time.

Many modifications in the above described embodiments of the invention can be carried out without departing from the scope thereof and, therefore, the scope of the present invention is intended to be limited only by the appended claims.

We claim:

1. A rapid eye movement detector for a sleep analyser comprising:
   means for combining a left eye EOG signal and a right eye EOG signal to provide an electro-oculogram signal,
   means for receiving the combined electro-oculogram (EOG) signal;

first means for selecting components of the combined EOG signal havina a predetermined rise time;

second means for selecting components of the combined EOG signal having a predetermined amplitude; and means for producing an output pulse each time a predetermined rise time component is coincident with a predetermined amplitude component, as an indication of rapid movement of the left and the right eyes in synchrony.

2. A rapid eye movement detector das claimed in claim 1 wherein the first selecting means is a bandpass filter having a real time frequency band from 1.3 to 5.4 Hz.

3. A rapid eye movement detector as claimed in claim 1 wherein the second selecting means includes a positive and a negative threshold discriminator, each connected to one input terminal of an or-gate.

* * * * *